United States Patent
Sharratt et al.

(10) Patent No.: US 12,357,968 B2
(45) Date of Patent: Jul. 15, 2025

(54) CATALYST ACTIVATION METHOD

(71) Applicant: Mexichem Fluor S.A. de C.V., San Luis Potosi (MX)

(72) Inventors: Andrew Sharratt, Runcorn (GB); Claire Rees, Runcorn (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 850 days.

(21) Appl. No.: 17/418,926

(22) PCT Filed: Jan. 16, 2020

(86) PCT No.: PCT/GB2020/050087
§ 371 (c)(1),
(2) Date: Jun. 28, 2021

(87) PCT Pub. No.: WO2020/148540
PCT Pub. Date: Jul. 23, 2020

(65) Prior Publication Data
US 2022/0062866 A1    Mar. 3, 2022

(30) Foreign Application Priority Data
Jan. 17, 2019  (GB) .................... 1900647

(51) Int. Cl.
*B01J 23/26*   (2006.01)
*B01J 23/06*   (2006.01)
*B01J 35/63*   (2024.01)
*B01J 35/64*   (2024.01)
*B01J 37/06*   (2006.01)
*B01J 37/14*   (2006.01)
*C07C 17/07*   (2006.01)

(52) U.S. Cl.
CPC .............. *B01J 23/26* (2013.01); *B01J 23/06* (2013.01); *B01J 35/633* (2024.01); *B01J 35/653* (2024.01); *B01J 37/06* (2013.01); *B01J 37/14* (2013.01); *C07C 17/07* (2013.01)

(58) Field of Classification Search
CPC . B01J 23/26; B01J 23/06; B01J 35/633; B01J 37/06; B01J 37/14; B01J 17/07; B01J 27/12; B01J 37/0236; B01J 35/647
See application file for complete search history.

(56) References Cited

U.S. PATENT DOCUMENTS

| | | |
|---|---|---|
| 231,840 A | 8/1880 | Neahous |
| 2,700,686 A | 1/1955 | Dickey et al. |
| 2,745,886 A | 5/1956 | Ruh et al. |
| 2,889,379 A | 6/1959 | Ruh et al. |
| 2,918,501 A | 12/1959 | Brehm et al. |
| 2,931,840 A | 4/1960 | Marquis |
| 2,996,555 A | 8/1961 | Rausch |
| 3,000,979 A | 9/1961 | Gibbs |
| 3,398,204 A | 8/1968 | Gallant |
| 3,674,665 A | 7/1972 | Cristol et al. |
| 3,739,036 A | 6/1973 | Valicenti et al. |
| 3,793,229 A | 2/1974 | Groppelli et al. |
| 4,093,670 A | 6/1978 | Ozawa et al. |
| 4,188,284 A | 2/1980 | Quick et al. |
| 4,220,608 A | 9/1980 | Feiring |
| 4,465,786 A | 8/1984 | Zimmer et al. |
| 4,798,818 A | 1/1989 | Baizer et al. |
| 5,227,350 A | 7/1993 | Scott et al. |
| 5,281,568 A | 1/1994 | Scott et al. |
| 5,672,803 A | 9/1997 | Smith et al. |
| 5,679,875 A | 10/1997 | Aoyama et al. |
| 5,763,711 A | 6/1998 | Ito |
| 5,811,603 A | 9/1998 | Elsheikh |
| 5,856,593 A | 1/1999 | Powell et al. |
| 5,986,151 A | 11/1999 | Van Der Puy |
| 6,111,150 A | 8/2000 | Sakyu et al. |
| 6,124,510 A | 9/2000 | Elsheikh et al. |
| 6,329,559 B1 | 12/2001 | Sievert et al. |
| 6,734,332 B1 | 5/2004 | Slaugh et al. |
| 2004/0049088 A1 | 3/2004 | LaCroix et al. |
| 2004/0167015 A1 | 8/2004 | Cann et al. |
| 2005/0038302 A1 | 2/2005 | Hedrick et al. |
| 2005/0090698 A1 | 4/2005 | Merkel et al. |
| 2005/0228202 A1 | 10/2005 | Nappa et al. |
| 2006/0122441 A1 | 6/2006 | Tung |
| 2006/0269484 A1 | 11/2006 | Knopeck et al. |
| 2007/0004585 A1 | 1/2007 | Amos et al. |

(Continued)

FOREIGN PATENT DOCUMENTS

| | | |
|---|---|---|
| CN | 1064628 A | 9/1992 |
| CN | 1078172 A | 11/1993 |

(Continued)

OTHER PUBLICATIONS

Atherton et al., Carbene Chemistry. Part II. Migration in Fluoroalkylcarbenes, J Chem. Soc., 1971; pp. 366-371.
Baklouti et al., Synthese D'Ethyleniques Monofluores, J. Fluorine Chem., 1981, pp. 181-190 (no English Equiv).
Banks et al., Preparation of 2,3,3,3-tetrafluoropropene from trifluoroacetylacetone and sulphur tetrafluoride, J. Fluorine Chem. vol. 82, 1997, pp. 171-174.
Boche et al., Stereospezifische Darstellung der (Z)-bzw. (E)-Isomeren von einigen Vinylfluoriden, Chem. Ber., vol. 114, 1981, pp. 4005-4009 (no English Equiv).

(Continued)

*Primary Examiner* — Jafar F Parsa
(74) *Attorney, Agent, or Firm* — Crowell & Moring LLP

(57) ABSTRACT

A method for activating a catalyst comprises the steps of: a) optionally drying the catalyst at a temperature of from 100° C. to 400° C.; b) treating the catalyst with a composition comprising HF at a temperature of from 0° C. to about 500° C.; c) treating the catalyst with a composition comprising an oxidant and optionally HF at a temperature of from about 100° C. to about 500° C.

24 Claims, No Drawings

(56) References Cited

U.S. PATENT DOCUMENTS

| | | | |
|---|---|---|---|
| 2007/0100175 A1 | 5/2007 | Miller et al. | |
| 2007/0112230 A1 | 5/2007 | Mukhopadhyay et al. | |
| 2007/0129579 A1 | 6/2007 | Wang et al. | |
| 2007/0197842 A1 | 8/2007 | Mukhopadhyay et al. | |
| 2008/0051611 A1 | 2/2008 | Wang et al. | |
| 2009/0118554 A1 | 5/2009 | Rao et al. | |
| 2009/0209792 A1 | 8/2009 | Sharratt et al. | |
| 2010/0072415 A1 | 3/2010 | Rao et al. | |
| 2010/0268002 A1 | 10/2010 | Nose et al. | |
| 2011/0060111 A1 | 3/2011 | Cann et al. | |
| 2011/0118513 A1 | 5/2011 | Smith et al. | |
| 2011/0160497 A1 | 6/2011 | Deur-Bert et al. | |
| 2013/0303812 A1 | 11/2013 | Birke et al. | |
| 2016/0221899 A1 | 8/2016 | Pigamo et al. | |
| 2017/0210686 A1 | 7/2017 | Pigamo et al. | |
| 2018/0370878 A1* | 12/2018 | Andre | B01J 37/24 |
| 2020/0148612 A1 | 5/2020 | Andre et al. | |

FOREIGN PATENT DOCUMENTS

| | | |
|---|---|---|
| CN | 1091057 A | 8/1994 |
| CN | 101175564 A | 5/2008 |
| CN | 102405203 A | 4/2012 |
| CN | 103328421 A | 9/2013 |
| CN | 104105681 A | 10/2014 |
| CN | 104475080 A | 4/2015 |
| CN | 104918700 A | 9/2015 |
| CN | 105688890 A | 6/2016 |
| CN | 106008147 A | 10/2016 |
| CN | 108367285 A | 8/2018 |
| DE | 1140928 | 12/1962 |
| DE | 2128341 | 12/1971 |
| DE | 69406525 T2 | 5/1998 |
| EP | 0393517 A2 | 10/1990 |
| EP | 0270006 B1 | 2/1991 |
| EP | 0436989 B1 | 7/1991 |
| EP | 0502605 A1 | 9/1992 |
| EP | 0644173 A1 | 3/1995 |
| EP | 0657408 A1 | 6/1995 |
| EP | 0726243 A1 | 8/1996 |
| EP | 0773061 A1 | 5/1997 |
| EP | 0752403 B1 | 1/2001 |
| EP | 0939071 B1 | 7/2003 |
| EP | 1350564 A1 | 10/2003 |
| EP | 1502906 A1 | 2/2005 |
| EP | 0957074 B2 | 1/2006 |
| EP | 1067106 B1 | 4/2006 |
| EP | 1900716 B1 | 10/2012 |
| EP | 1877181 B1 | 6/2015 |
| EP | 1918269 B2 | 1/2019 |
| EP | 3509740 | 7/2019 |
| EP | 3509741 | 7/2019 |
| EP | 3330244 B1 | 1/2020 |
| FR | 2342952 | 9/1977 |
| FR | 2740994 A1 | 5/1997 |
| GB | 1407696 | 9/1975 |
| GB | 1415649 | 11/1975 |
| GB | 2011463 A | 7/1979 |
| GB | 2162082 A | 1/1986 |
| GB | 1615197.9 | 10/2016 |
| JP | S54-116004 | 9/1979 |
| JP | H02280837 | 11/1990 |
| JP | H04-346948 | 12/1992 |
| JP | H 05-220400 A | 8/1993 |
| JP | 07-206728 | 8/1995 |
| JP | H1114002 | 5/1999 |
| JP | 2006/111611 A | 4/2006 |
| JP | 2008-534276 A | 8/2008 |
| JP | 2011-517681 A | 6/2011 |
| JP | 2012-501826 A | 1/2012 |
| JP | 2016053064 A | 4/2016 |
| KR | 10-20110004431 | 1/2011 |
| KR | 10-20110004434 | 1/2011 |
| KR | 10-1343618 | 12/2013 |
| KR | 10-1343471 | 1/2014 |
| RU | 2322291 C1 | 4/2008 |
| RU | 2402378 C1 | 10/2010 |
| RU | 2431524 C2 | 10/2011 |
| RU | 2555842 C1 | 7/2015 |
| WO | WO 1993/04025 A1 | 3/1993 |
| WO | WO 1993/16798 | 9/1993 |
| WO | WO 1993/25507 A1 | 12/1993 |
| WO | WO 1994/06558 | 3/1994 |
| WO | WO 1996/11896 | 4/1996 |
| WO | WO 1997/05089 | 2/1997 |
| WO | WO 1998/10862 | 3/1998 |
| WO | WO 1998/33756 | 8/1998 |
| WO | WO 1998/37043 | 8/1998 |
| WO | WO 1999/62857 | 12/1999 |
| WO | WO 00/24696 A1 | 5/2000 |
| WO | WO 2000/24696 A1 | 5/2000 |
| WO | WO 2004/018095 A1 | 3/2004 |
| WO | WO 2005/012212 A2 | 2/2005 |
| WO | WO 2005/023984 A2 | 3/2005 |
| WO | WO 2005/037431 A1 | 4/2005 |
| WO | WO 2005/037743 A1 | 4/2005 |
| WO | WO 2005/037744 A1 | 4/2005 |
| WO | WO 2005/042451 A2 | 5/2005 |
| WO | WO 2005/108332 A1 | 11/2005 |
| WO | WO 2005/108333 A1 | 11/2005 |
| WO | WO 2005/108334 A1 | 11/2005 |
| WO | WO 2006/106353 | 10/2006 |
| WO | WO 2006/106353 A1 | 10/2006 |
| WO | WO 2007/056194 A1 | 5/2007 |
| WO | WO 2007/079431 A2 | 7/2007 |
| WO | WO 2007/079435 A2 | 7/2007 |
| WO | WO 2007/145171 A1 | 12/2007 |
| WO | WO 2008/002500 A1 | 1/2008 |
| WO | WO 2008/008350 A2 | 1/2008 |
| WO | WO 2008/030443 A1 | 3/2008 |
| WO | WO 2008/040969 A2 | 4/2008 |
| WO | WO 2008/054781 A1 | 5/2008 |
| WO | WO 2008/054782 A1 | 5/2008 |
| WO | WO 2008/075017 A2 | 6/2008 |
| WO | WO 2009/125199 A2 | 10/2009 |
| WO | WO 2009/125200 A2 | 10/2009 |
| WO | WO 2009/125201 A2 | 10/2009 |
| WO | WO 2009/140563 A1 | 11/2009 |
| WO | WO 2010/026382 | 3/2010 |
| WO | WO 2010/026382 A2 | 3/2010 |
| WO | WO 2010/026383 A2 | 3/2010 |
| WO | WO 2011/140013 A1 | 11/2011 |
| WO | WO 2015/046345 A1 | 4/2015 |
| WO | WO 2018/046927 A1 | 3/2018 |
| WO | WO 2018/046928 A1 | 3/2018 |

OTHER PUBLICATIONS

Burton et al., Preparation of E-1,2,3,3,3-pentafluoropropene, Z-1,2,3,3,3-pentafluoropropene and E-1-iodopentafluoropropene, J. Fluorine Chem. 44 (1989) (1), 189; pp. 167-174.

Catalysts Studies on Fluorination from 2-chloro-3,3,3-trifluoropropene to tetrafluoropropene (HFC-1234yf, HFC-1234ze), Zunyun Xie, "Chinese Master's Theses Full-text Database Engineering Science and Technology I", No. 3, 2014, B014-232.

Design and Preparation of Solid Catalyst, PAN Lvrang, pp. 137-138, Nankai University Press, 5 pgs.

English Translation of Office Action for Chinese application 201780061867.X, issued Jun. 17, 2021, 17 pgs.

English Translation of Office Action for Chinese application 201780065320.7, issued Jul. 2, 2021, 16 pgs.

English translation of Patent No. RU2555842, Jul. 10, 2015, pp. 1019.

Haszeldine, Addition of Free Radicals to Unsaturated Systems. Part XXI. Reactions of 1H-Pentafluoropropene with Bromine, Hydrogen Bromide, and Tri-fluoroiodomethane under Free-radical Conditions, J. Chem. Soc. Perkin Trans. 1, 1974, pp. 1303-1307.

Haszeldine et al., Free-radical Additions to Unsaturated Systems. Part XVII. Reaction of Trifluoroiodomethane with Mixtures of Ethylene and Vinyl Fluoride and of Ethylene and Propene, J. Chem. Soc. 1970, pp. 414-421.

(56) References Cited

OTHER PUBLICATIONS

Haszeldine et al., Fluoro-olefine Chemistry. Part X. Some Additions to 1-Fluoropropene under Ionic and Free-radical Conditions, J. Chem. Soc Perkin Trans. 1, 1976; pp. 2349-2353.
Haszeldine et al., Carbene Chemistry. Part 11. Insertion Reactions of 1,2,2-Trifluoroethylidenen into Carbon-Hydrogen Bonds of Alkanes, Cycloalkanes, and Diethyl Ether, J. Chem. Soc. Perkin Trans. 1, 1979; pp. 1943-1947.
Haszeldine et al., J.Chem. Soc. "Fluoro-olefins. Pt. II, Synthesis and Reactions of Some 3:3:3-trihalogenpropenes", 1953; pp. 3371-3378.
International Search Report for International application No. PCT/GB2017/052616 dated Dec. 22, 2017, 5 pgs.
Joyce et al., Free Radical-initiated Reaction of Ethylene with Carbon Tetrachloride, J. Am Chem. Soc., 1948; pp. 2529-2532.
M.B. Smith and J. March, Advanced Organic Chemistry, Mechanisms and Structure, 5$^{th}$ Edition, 2001, John Wiley & Sons, Inc., p. 1195.
Notice of Opposition in Europe Application No. 17768203.6, dated Aug. 9, 2021, 32 pages.
Notice of Opposition in Europe Application No. 17768204.4, dated Aug. 9, 2021, 34 pages.
Office Action for Chinese application 201780061867.X, issued Jun. 17, 2021, English Translation, 17 pgs.
Office Action for Chinese application 201780065320.7, issued Jul. 2, 2021, 21 pgs.
Final Office Action from U.S. Appl. No. 16/331,450 issued Mar. 18, 2022, 10 pgs.
Petrov et al., "Effect of Chromium Content on the Properties of a Alumina-Chromia Catalyst in Tetrachlorethylene Hydrofluorination", AIP Conference Proceedings 1772.030009 (2016), (cited Oct. 13, 2016), 6 pages.
Rama Rao et al., "Influence of Method of Preparation on Pore Structure and Deydrogenation of Activity of Chromia Catalysts", Indian Journal of Chemistry, dated Aug. 1996, vol. 35 A, Aug. 1996, pp. 656-659, 4 pgs.
Rouquerol et al., "Recommendations for the Characterization of Porous Solids (Technical Report)", Pure & Appl. Chem. vol. 66, No. 8, 1994, pp. 1739-1758, International Union of Pure and Applied Chemistry, 20 pages.
Search Report from corresponding Great Britain Application No. GB1615197.9 dated Mar. 8, 2017, 4 pgs.
Sianesi et al., Fluoroolefins—Report 1 Cis and Trans 1, 2, 3, 3, 3-pentalfluoropropylene Soc Montecatini Milan, ann Chim (Rome), 55 (8-9), 1965 pp. 850-861.
Thesis Hadar Rotter, "Development & Testing the Nanostructured Transition Metal Oxides in Combustion of Volatile Organic Compounds," Mar. 2006, 9 pages.
Thommes et al., Physisorption of Gases, with Special Reference to the Evaluation of Surface area and Pore Size Distribution (IUPAC Technical Report), Pure Appl. Chem. 2015, vol. 87, Nos. 9-10, pp. 1051-1069, Aug. 2015, 19 pages.
Written Opinion cited in PCT/GB2017/052616 dated Dec. 22, 2017.
Baklouti et al., Synthese D'Ethylenqiues Monofluores, J. Fluorine Chem., 1981, pp. 181-190, with English summary p. 181.
Boche et al., Stereospezifische Darstellung der (Z)-bzw. (E)-Isomeren von einigen Vinylfluoriden, Chem. Ber., vol. 114, 1981, pp. 4005-4009, with English abstract p. 4005.
Design and Preparation of Solid Catalyst, PAN Lvrang, pp. 137-138, Nankai University Press, 5 pgs., with English translation of the main content.
International Search Report for corresponding International Application PCT/GB2020/050087 mailed Aug. 7, 2020, 7 pgs.
Written Opinion of the International Searching Authority for corresponding International Application PCT/GB2020/050087 mailed Aug. 7, 2020, 11 pgs.
International Preliminary Report on Patentability in Application No. PCT/GB2020/050087, dated Jun. 16, 2021, 12 pages.
Combined Search and Examination Report in Great Britain Application No. 1900647.7, dated Jul. 22, 2019, 6 pages.
English translation of Chinese Office Action for corresponding Chinese Application No. 202080009662.9, issued Jan. 10, 2024, 17 pgs.
English translation of Japanese Office Action for corresponding Japanese Application No. 2021-541109, mailed Dec. 27, 2023, 3 pgs.
English Translation of First Office Action in Chinese Application No. 202080009662.9, dated Feb. 15, 2023 (16 pages).
Xing, L, et al., "In Situ Raman Spectroscopy Studies on Chromium Oxide Catalyst in an Anhydrous Hydrogen Fluoride Atmosphere", *Journal of Raman Spectroscopy*, vol. 42, Issue 5, 2011, pp. 1095-1099 (5 pages).
Chen, Jun, "A Preparation Method of 1,1,1,2,2-pentafluoroethane", *Organo-Fluorine Industry*, Issue 4, Apr. 15, 2009, pp. 55-62 (8 pages).
Chen, Jun, "A Preparation Method fo 1,1,1,2,2-pentafluoroethane", *Organo-Fluorine Industry*, Issue 4, Apr. 15, 2009, Translation of Abstract (1 page).

\* cited by examiner

CATALYST ACTIVATION METHOD

CROSS-REFERENCE TO RELATED APPLICATIONS

This application is the U.S. National Stage application of PCT Application No. PCT/GB2020/050087, filed on Jan. 16, 2020, titled METHOD, designating the United States, which claims priority to Great Britain Application No. 1900647.7, filed on Jan. 17, 2019, the contents of which are each incorporated herein by reference in their entirety.

The present invention relates to a method for activating a catalyst and to a process that uses said catalyst.

The listing or discussion of a prior published document in this specification should not necessarily be taken as an acknowledgement that the document is part of the state of the art or is common general knowledge.

Halocarbon-based compounds, particularly fluorocarbon-based compounds are currently used in a large number of commercial and industrial applications, such as propellants, blowing agents and heat transfer fluids. The interest in and use of fluorine-based compounds, particularly (hydro)fluoroolefins, as heat transfer fluids has increased as new refrigerants are sought.

Fluorination and/or hydrofluorination steps are also common in the manufacturing processes of (hydro)fluoroalkenes. Such processes may be performed by contacting HF with one or more (hydro)haloalkenes or (hydro)haloalkanes, preferably in the presence of a catalyst.

Fluorination and/or hydrofluorination steps involve reacting a starting material with a fluorinating agent (e.g. hydrogen fluoride) to introduce one or more fluorine atoms to the starting material. Such processes comprise addition of one or more fluorine atoms to the starting material and/or substitution of one or more atoms of the starting material with one or more fluorine atoms.

Typically, fluorination and/or hydrofluorination steps are performed industrially under catalysis. Catalysts suitable for use in such processes are often compounds of transition metals, for instance transition metal oxides and/or halides. Preferred examples of such catalysts include those based on chromia, frequently containing another metal, such as zinc.

Prior to the fluorination and/or hydrofluorination step, the catalyst is usually subjected to an activation treatment to achieve the desired catalytic performance. Normally, this involves treating the catalyst with hydrogen fluoride, at an elevated temperature. Frequently, the activation treatments are preceded by other steps, such as drying or heating the catalyst in inert atmosphere, in other words "calcination".

WO2010/026382 discloses such methods for treating a catalyst for use prior to engaging a catalyst in fluorination of 1-chloro-2,2,2-trifluoroethane to 1,1,1,2-tetrafluoroethane (R-134a). In EP 06726692, a catalyst is treated prior to contacting the catalyst with hydrogen fluoride and perchloroethylene to yield pentafluoroethane.

However, it has been found that these activation treatments are insufficient to successfully activate catalysts for the processes of fluorinating and/or hydrofluorinating halogenated hydrocarbons with longer carbon chains, particularly $C_{3-7}$(hydro)haloalkenes. The catalysts have been found to suffer from slow and complex activation behaviour, lack of stability, as well as mass transport limitations. All these limitations result in poor catalytic performance. These problems have been observed in processes of commercial interest, particularly in conversion of 2-chloro-3,3,3-trifluoropropene (1233xf) to 2,3,3,3-tetrafluoropropene (1234yf).

Therefore, there exists a need for developing improved methods for activating fluorination catalysts.

Further, catalytic reactions involving halocarbons have a number of problems in use, one of which is that industrial scale processes subject the catalysts to extreme temperatures and pressures, numerous regenerations and corrosive reagents. The skilled person will know that over the lifetime of an industrial catalyst the activity is steadily reduced, and the catalyst must eventually be replaced in an expensive procedure.

There is therefore a need for catalysts with improved stability and comparable or improved activity and selectivity relative to existing catalysts.

According to a first aspect of the invention there is provided a method for activating a catalyst comprising the steps of:
  a) optionally drying the catalyst at a temperature of from 100° C. to 400° C.;
  b) treating the catalyst with a composition comprising HF at a temperature of from 100° C. to about 500° C.;
  c) treating the catalyst with a composition comprising an oxidant and optionally HF at a temperature of from about 100° C. to about 500° C.

The oxidant is preferably selected from air, oxygen ($O_2$), chlorine ($Cl_2$), chlorine monofluoride (ClF), nitrogen trifluoride ($NF_3$) and combinations thereof.

The molar ratio of HF to oxidant is preferably from 1:20 to 20:1, more preferably from 15:1 to 1:3, and most preferably from 11:1 to 1:1.

Step (b) and/or (c) is preferably carried out at a pressure of from 0.1 bara to 20 bara, more preferably from 3 bara to 10 bara.

Step (b) and/or (c) is preferably carried out over an extended period. The period will be recognised by the skilled person as being scale dependent. At laboratory scale a duration of between about 5 hours and about 65 hours is preferred, more preferably between about 8 hours and about 55 hours. In a commercial operating plant this timing may require extension. In a commercial operating plant, a duration of between about 24 hours and about 168 hours is preferred. The length of time employed for step (b) and for step (c) may be the same or different.

Step (b) and/or (c) is preferably carried out at a temperature of from about 200° C. to about 500° C., more preferably from about 250° C. to about 475° C., more preferably from about 300° C. to about 460° C., such as from about 310° C. to about 450° C. The temperature of step (b) and step (c) may be the same or different.

According to a second aspect of the invention there is provided a method for activating a catalyst comprising the steps of:
  (a) optionally drying the catalyst at a temperature of from 100'C to 400° C.;
  (b) treating the catalyst with a composition comprising HF at a temperature of from 500° C. to about 700° C.

In the method of the second aspect of the invention, step (b) is preferably carried out at a pressure of from 0.1 bara to 20 bara, more preferably from 3 bara to 10 bara.

In the method of the second aspect of the invention, step (b) is preferably carried out over an extended period. The period will be recognised by the skilled person as being scale dependent. At laboratory scale a duration of between about 5 hours and about 65 hours is preferred, more preferably between about 8 hours and about 55 hours. In a commercial operating plant this timing may require extension. In a commercial operating plant a duration of between about 24 hours and about 168 hours is preferred. It will be appreciated that the length of time employed for step (b) and for step (c) may be the same or different.

In the method of the second aspect of the invention, step (b) is preferably carried out at a temperature of from about 500° C. to about 600° C., most preferably about 520° C.

Preferably the catalyst comprises chromia and at least one additional metal or compound thereof, wherein the at least one additional metal is selected from Li, Na, K, Ca, Mg, Cs, Sc, Al, Y, Ti, Zr, Hf, V, Nb, Ta, Cr, Mo, W, Mn, Re, Fe, Ru, Co, Rh, Ir, Ni, Pd, In, Pt, Cu, Ag, Au, Zn, La, Ce and mixtures thereof.

In a further aspect, there is provided a method for producing 2,3,3,3-tetafluoropropene (1234yf) from a precursor in the presence of a catalyst activated in accordance with the first aspect of the invention. This additional metal or compound thereof can also be referred to as a promoter. Preferably, the at least one additional metal is selected from Li, Na, K, Ca, Mg, Cs, Cr, Zr, Nb, Pd, Ta, Zn, V, Mo, Ni, Co, In, Fe, Cu and mixtures thereof, even more preferably the additional metal is zinc. The skilled person would appreciate that in catalysis in general, catalytic activity is understood to be proportional to the available surface area of the catalyst. It is to be expected that increasing the opportunity for the reagents to interact with the surface of the catalyst will improve the rate of conversion. However, in contrast to established teaching, the present inventors have surprisingly found that increasing the pore volume and average pore diameter, which may inherently reduce a catalyst's surface area, increases both the stability and the activity of the catalyst.

Without wishing to be bound by theory, it is believed that this is a result of the increased mass transfer through the catalyst and that this effect is more pronounced for $C_3$ compounds than $C_2$ compounds. Also, without wishing to be bound by theory, it is believed that the wider pore diameters of the present invention allow the catalyst in use to assume more quickly an effective pore structure for producing (hydro)haloalkenes such as hydrofluoropropenes.

The pore structure of solid porous materials can be determined by several methods, one of the most commonly used is the adsorption and desorption of $N_2$, based on the BET theory (Brunauer, Emmett and Teller) of the adsorption of multilayers of condensed gases onto solid surfaces, and the evaporation (desorption) of the adsorbed gas during desorption. Nitrogen is a common adsorbate for probing the micro and mesoporous regions. From the adsorption and desorption isotherms, the following can be calculated: BET surface area from the adsorption of a monolayer of $N_2$, total pore volume taken from the amount of nitrogen adsorbed at $P/P°=0.99$ and average pore diameters can be determined using different calculations either based on the BET theory or that of BJH (Barrett, Joyner and Halenda), either from the adsorption or desorption data. Preferably, the total pore volume of the catalyst is equal to or greater than 0.35 cm$^3$/g or 0.4 cm$^3$/g, such as 0.45 cm$^3$/g, 0.5 cm$^3$/g, 0.55 cm$^3$/g or even 0.6 cm$^3$/g when measured by $N_2$ adsorption porosimetry.

Preferably, the average pore width of the catalyst is greater than or equal to 100 Å, e.g. greater than or equal to 110 Å or greater than or equal to 120 Å when measured by $N_2$ BET adsorption porosimetry.

Preferably, the average pore width of the catalyst is greater than or equal to 130 Å, e.g. greater than or equal to 140 Å, greater than or equal to 150 Å or greater than or equal to 170 Å when measured by $N_2$ BJH adsorption porosimetry.

Preferably, the average pore width of the catalyst is greater than or equal to 90 Å, e.g. greater than or equal to 100 Å, greater than or equal to 110 Å or greater than or equal to 120 Å when measured by $N_2$ BJH desorption porosimetry.

It is appreciated that other methods of porosimetry measurements are known to the skilled person.

The catalysts preferably have a surface area from 5 to 250 m$^2$/g following activation, Typically, the catalysts have a surface area of 40 to 50 m$^2$/g following activation.

Preferably, the catalyst is provided in the form of a pellet or pellets comprising a plurality of catalyst particles. Such catalyst particles may be pressed together, for example under load, to form the pellets. The pellets may comprise one or more further materials. For example, the pellets may include graphite, preferably in an amount of from about 0.5 wt % to about 10 wt %, e.g. from about 1 wt % to about 5 wt %. Preferably, the pellets have a longest dimension from about 1 mm to about 100 mm. In some embodiments, the pellets may have a longest dimension of about 1 mm to about 10 mm, for example from about 3 mm to about 5 mm.

Preferably, the catalyst comprises at least 80 wt % (for example at least 85 wt %, at least 90 wt %, at least 92 wt %, at least 93 wt %, at least 94 wt %, at least 95 wt % or at least 96 wt %) chromia. Advantageously, the catalyst may be a zinc/chromia catalyst. By the term "zinc/chromia catalyst" we mean that the metal oxide catalyst comprises chromium or a compound of chromium and zinc or a compound of zinc.

The total amount of the zinc or a compound of zinc present in the zinc/chromia catalysts of the invention is typically from about 0.01% to about 25%, preferably 0.1% to about 25%, conveniently 0.01% to 6% of the catalyst; and in some embodiments preferably 0.5% by weight to about 25% by weight of the catalyst, preferably from about 1 to 10% by weight of the catalyst, more preferably from about 2 to 8% by weight of the catalyst, for example about 3 to 6% by weight of the catalyst.

In further preferred embodiments, the additional metal compound may comprise indium (e.g. in the form $In_2O_3$) and/or zirconium (e.g. in the form $ZrO_2$).

Additional metals or compounds thereof are typically present from about 0.01% to about 25%, preferably 0.1% to about 25%, conveniently 0.01% to 6% by weight of the catalyst; and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst.

In other embodiments, the catalyst may be an alumina catalyst with one or more promoters selected from platinum, iron, chromium and zinc. The total amount of promoter is typically from about 0.1 to about 60% by weight of the catalyst, preferably from about 0.5 to about 50% by weight of the catalyst, such as 0.5% by weight to about 25% by weight of the catalyst, or from about 1 to 10% by weight of the catalyst. In such embodiments it is preferred that the catalyst comprises at least 80 wt % (for example at least 85 wt %, at least 90 wt %, at least 92 wt %, at least 93 wt %, at least 94 wt %, at least 95 wt % or at least 96 wt %) chromia. In some embodiments, the catalyst may be in fluorinated form. For example, the catalyst may have been fluorinated by treatment with HF at elevated temperature.

Many of these preferred features may be combined into a preferred embodiment. Thus, according to a third aspect of the invention there is provided a method for activating a catalyst, wherein the catalyst comprises a chromia catalyst, with zinc oxide present in the catalyst at a level of from 1% wt to 10% wt, wherein the catalyst has a total pore volume equal to or greater than 0.3 cm$^3$/g and a mean pore diameter greater than or equal to 100 Å, wherein the pore volume is measured using $N_2$ adsorption porosimetry and the mean pore diameter is measured using $N_2$ BET adsorption porosimetry; comprising the steps of:

a) optionally drying the catalyst at a temperature of from 100° C. to 400° C.;

b) treating the catalyst with a composition comprising HF at a temperature of from 100° C. to about 500° C.;

c) treating the catalyst with a composition comprising an oxidant and optionally HF at a temperature of from about 100° C. to about 500° C.

Preferred features of the first and second aspects of the invention shall; be taken to apply mutatis mutandis to the third aspect of the invention.

Preferably the zinc oxide/chromia catalyst used in the present invention may be amorphous. By this we mean that the catalyst does not demonstrate any substantial crystalline characteristics when analysed by, for example, X-ray diffraction.

Alternatively, the zinc oxide/chromia catalyst used in the present invention may be partially crystalline. By this we mean that from 0.1 to 50% by weight of the catalyst is in the form of one or more crystalline compounds of chromium and/or one or more crystalline compounds of zinc. If a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of chromium and/or one or more crystalline compounds of zinc.

It is appreciated that during use in a reaction the degree of crystallinity may change. Thus it is possible that a catalyst having a degree of crystallinity as defined above before use in a reaction and will have a degree of crystallinity outside these ranges during or after use in a reaction.

The catalysts preferably have a surface area from 5 to 250 $m^2/g$ following activation, Typically, the catalysts have a surface area of 40 to 50 $m^2/g$ following activation.

The present invention also provides a method of preparing a catalyst, said method comprising the steps of:

a) preparing a metal salt solution and a hydroxide solution;

b) combining the solutions at a pH of greater than 7.5 in order to precipitate the metal hydroxide(s);

c) drying the precipitated metal hydroxides;

d) calcining the metal hydroxide(s) to form the metal oxide(s).

Preferably, the metal salt comprises a nitrate salt such as a hydroxide nitrate salt. In preferred embodiments, the metal salt comprises chromium, and may comprise a chromium nitrate salt such as $Cr(OH)(NO_3)_2$. The hydroxide solution may comprise ammonium hydroxide ($NH_4OH$). Advantageously, step b) is carried out at a pH of greater than 8. Preferably, step b) is carried out at a pH of greater than or equal to 8.1, 8.2, 8.3; 8.4 or 8.5.

In a further aspect of the invention, there is provided a process for fluorinating a $C_{2-3}$ hydrohalocarbon species, comprising contacting the species with a catalyst according to the invention. This is typically carried out in the presence of HF. For the avoidance of doubt, the term $C_{2-3}$ hydrohalocarbon includes saturated or unsaturated compounds with a two or three carbon chain and containing one or more atoms of hydrogen and a halogen (F, Cl, Br, I). In preferred embodiments, the hydrohalocarbon species comprises a $C_3$ hydrohalocarbon species.

An example of such a process comprises contacting trichloroethylene with the catalyst in the presence of HF to produce 1,1,1,2-tetrafluoroethane (134a), the conversion of 1,1,1,2,3-pentachloropropane (240db) to 2-chloro-3,3,3-trifluoropropene (1233xf), the conversion of 1233xf to 2,3,3,3-tetrafluoropropene (1234y) and/or 1,1,1,2,2-pentfluoropropane (245cb), the conversion of 1,1,1,3-tetrachloropropane (250fb) to 3,3,3-trifluoropropene (1243zf), or the conversion of 2,3-dichloro-1,1,1-trifluoropropane (243db) to 1233xf and/or 1234yf.

In another aspect of the invention, there is provided a process for dehydrohalogenating a $C_{2-3}$ hydrohalocarbon species (preferably a $C_3$ hydrohalocarbon species), comprising contacting the species with a catalyst, such as contacting a hydro(halo)fluoropropane with the catalyst to produce a fluoropropene, preferably a tetrafluoropropene (1234) such as 1234ze ((E) or (Z)) or 1234yf. Advantageously, this may include the conversion of 245cb and/or 1,1,1,2,3-pentafluoropropane (245eb) to 2,3,3,3-tetrafluoropropene (1234yf) and/or 1,3,3,3-tetrafluoropropene (1234ze), the conversion of 1,1,1,3,3-pentafluoropropane (245fa) to 1234ze or the conversion of 1-chloro-1,3,3,3-tetrafluoropropane to 1-chloro-3,3,3-trifluoropropene (1233zd) or 1234ze. In a further aspect of the invention, there is provided a process for eliminating HF or from a saturated $C_{2-3}$ hydrohalocarbon species (preferably a $C_3$ hydrohalocarbon species), comprising contacting the species with a catalyst In another aspect of the invention, there is provided a process for adding HF to an unsaturated $C_{2-3}$ hydrohalocarbon species (preferably a $C_3$ hydrohalocarbon species), comprising contacting the species with a catalyst.

The processes may be conducted in the liquid or the vapour phase but are preferably conducted in the vapour phase. The process may be carried out at atmospheric, sub- or super atmospheric pressure, typically at from 0 to about 30 bara, preferably from about 1 to about 20 bara, such as 15 bara.

Typically, the vapour phase process is carried out a temperature of from about 100° C. to about 500° C. (e.g. from about 150° C. to about 500° C. or about 100 to about 450° C.). Preferably, the process is conducted at a temperature of from about 150° C. to about 450° C., such as from about 150° C. to about 400° C., e.g. from about 175° C. to about 300° C. Lower temperatures may also be used in the conversion of 250fb to 1243zf, such as from about 150° C. to about 350° C., e.g. from about 150° C. to about 300° C. or from about 50° C. to about 250° C.

The processes typically employ a molar ratio of HF:organics of from about 1:1 to about 100:1, such as from about 3:1 to about 50:1, e.g. from about 4:1 to about 30:1 or about 5:1 or 6:1 to about 20:1 or 30:1. The reaction time for the process generally is from about 1 second to about 100 hours, preferably from about 10 seconds to about 50 hours, such as from about 1 minute to about 10 or 20 hours. In a continuous process, typical contact times of the catalyst with the reagents are from about 1 to about 1000 seconds, such from about 1 to about 500 seconds or about 1 to about 300 seconds or about 1 to about 50,100 or 200 seconds.

EXAMPLES

Catalyst Activation Examples 3 ml of chromia catalyst particles (size range from 0.5 mm to 1.0 mm) containing 3 wt % ZnO was dried by heating at 250° C. for 4 hours under a nitrogen atmosphere (60 ml/min) at 1 Bara.

The catalyst was subjected to a first activation step at 380° C. for 16 hours under a HF atmosphere (30 ml/min).

The catalyst was subjected to a second activation step under the conditions as outlined below.

| Example | Temperature | Duration | Second Activation Step Activants |
|---|---|---|---|
| 1 | 380° C. | 16 hours | Air and HF (25 ml/min each) |
| 2 | 380° C. | 40 hours | Air and HF (25 ml/min each) |
| 3* | 380° C. | 16 hours | Air and HF (25 ml/min each) |
| 4* | 380° C. | 40 hours | Air and HF (25 ml/min each) |

*the chromia contained 6.5 wt % ZnO.

| Comparative Example | Temperature | Duration | Second Activation Step Activants |
|---|---|---|---|
| A | 380° C. | 16 hours | Nitrogen and HF (25 ml/min each) |
| B | 380° C. | 16 hours | Nitrogen and Air (25 ml/min each) |
| C | 380° C. | 16 hours | Nitrogen (50 ml/min) |
| D | 380° C. | 40 hours | Nitrogen and HF (25 ml/min each) |
| E | 380° C. | 40 hours | Nitrogen and Air (25 ml/min each) |
| F | 380° C. | 40 hours | Nitrogen (50 ml/min) |
| G* | 380° C. | 16 hours | Nitrogen and HF (25 ml/min each) |
| H* | 380° C. | 16 hours | Nitrogen and Air (25 ml/min each) |
| I* | 380° C. | 16 hours | Nitrogen (50 ml/min) |
| J* | 380° C. | 40 hours | Nitrogen and HF (25 ml/min each) |
| K* | 380° C. | 40 hours | Nitrogen and Air (25 ml/min each) |
| L* | 380° C. | 40 hours | Nitrogen (50 ml/min) |

*the chromia contained 6.5 wt % ZnO.

Catalytic Examples

The activated catalyst was contacted with 2-chloro-3,3,3-trifluoropropene (1233xf) (1 ml/min) and hydrogen fluoride (25 ml/min) in a reactor. The cycle time was between about 21 hours and about 28 hours. The pressure was 1 bara.

The data generated was in the form of reactor off-gas (ROG) compositions for the feed (1233xf) and main reaction products 2,3,3,3-tetrafluoropropene (1234yf) and 1,1,1,2,2-pentafluoropropane (245cb).

Results

| Catalyst | Cycle time (hrs) | 1233xf (mol %) | 1234yf (mol %) | 245cb (mol %) | $k'_{xf}$ |
|---|---|---|---|---|---|
| 1 | 0.5 | 23.63 | 59.29 | 17.08 | 1.12 |
|  | 2.06 | 28.71 | 56.03 | 15.26 | 0.94 |
|  | 3.38 | 30.96 | 54.29 | 14.76 | 0.94 |
|  | 4.7 | 31.10 | 54.30 | 14.60 | 0.93 |
|  | 21.1 | 36.07 | 50.37 | 13.56 | 0.83 |
| 2 | 0.83 | 29.14 | 55.15 | 15.71 | 1.01 |
|  | 3.12 | 31.35 | 53.63 | 15.01 | 0.95 |
|  | 4.86 | 31.64 | 53.50 | 14.85 | 0.99 |
|  | 21.38 | 34.74 | 51.14 | 14.11 | 0.81 |
|  | 27 | 36.24 | 49.98 | 13.77 | 0.76 |
| 3* | 1.13 | 28.74 | 53.59 | 17.67 | 1.03 |
|  | 3.65 | 31.79 | 51.38 | 16.82 | 0.97 |
|  | 5.3 | 32.88 | 50.62 | 16.50 | 0.90 |
|  | 22.13 | 47.94 | 39.63 | 12.43 | 0.47 |
|  | 24.43 | 50.55 | 37.71 | 11.74 | 0.43 |
| 4* | 0.76 | 29.13 | 54.26 | 16.61 | 0.94 |
|  | 2.86 | 33.55 | 51.43 | 15.01 | 0.81 |
|  | 23.65 | 43.10 | 44.36 | 12.54 | 0.60 |

| Catalyst | Treatment time (hrs) | Cycle time (hrs) | 1233xf (mol %) | 1234yf (mol %) | 245cb (mol %) | $k'_{xf}$ |
|---|---|---|---|---|---|---|
| A | 16 | 0.82 | 31.83 | 52.99 | 15.18 | 0.82 |
|  | 16 | 2.23 | 34.14 | 51.25 | 14.60 | 0.72 |
|  | 16 | 3.56 | 36.42 | 49.65 | 13.93 | 0.71 |
|  | 16 | 4.88 | 37.60 | 48.72 | 13.68 | 0.69 |
|  | 16 | 21.35 | 44.83 | 43.05 | 12.11 | 0.54 |
| B | 16 | 1.06 | 27.82 | 55.37 | 16.81 | 0.89 |
|  | 16 | 2.48 | 33.60 | 50.98 | 15.43 | 0.73 |
|  | 16 | 3.82 | 39.54 | 46.55 | 13.91 | 0.60 |
|  | 16 | 5.12 | 45.62 | 41.95 | 12.44 | 0.48 |
|  | 16 | 21.52 | 78.37 | 16.83 | 4.78 | 0.13 |
| C | 16 | 1.25 | 57.58 | 32.09 | 10.33 | 0.30 |
|  | 16 | 2.65 | 68.17 | 24.40 | 7.42 | 0.20 |
|  | 16 | 3.98 | 72.70 | 21.06 | 6.25 | 0.16 |
|  | 16 | 5.32 | 74.48 | 19.71 | 5.81 | 0.16 |
|  | 16 | 21.75 | 77.31 | 17.62 | 5.07 | 0.14 |
| D | 40 | 0.5 | 36.04 | 49.97 | 13.99 | 0.71 |
|  | 40 | 2.92 | 37.61 | 48.63 | 13.75 | 0.76 |
|  | 40 | 4.7 | 38.02 | 48.42 | 13.56 | 0.73 |
|  | 40 | 21.1 | 41.74 | 45.50 | 12.76 | 0.62 |
|  | 40 | 26.78 | 42.29 | 45.11 | 12.59 | 0.62 |
| E | 40 | 1.38 | 34.67 | 49.35 | 15.98 | 0.77 |
|  | 40 | 3.48 | 47.01 | 40.08 | 12.89 | 0.48 |
|  | 40 | 5.32 | 63.56 | 27.69 | 8.75 | 0.25 |
|  | 40 | 21.78 | 79.24 | 16.12 | 4.63 | 0.12 |
|  | 40 | 27.45 | 79.36 | 16.05 | 4.59 | 0.12 |
| F | 40 | 1.22 | 52.51 | 36.37 | 11.12 | 0.38 |
|  | 40 | 3.26 | 62.89 | 28.61 | 8.49 | 0.25 |
|  | 40 | 5.12 | 66.87 | 25.64 | 7.49 | 0.22 |
|  | 40 | 21.56 | 73.37 | 20.69 | 5.94 | 0.17 |
|  | 40 | 27.26 | 73.61 | 20.47 | 5.92 | 0.17 |
| G | 16 | 0.92 | 27.64 | 54.83 | 17.51 | 1.04 |
|  | 16 | 3.47 | 31.48 | 52.23 | 16.29 | 0.96 |
|  | 16 | 5.02 | 32.32 | 51.65 | 16.03 | 0.89 |
|  | 16 | 21.92 | 46.46 | 41.07 | 12.47 | 0.49 |
|  | 16 | 24.23 | 48.78 | 39.37 | 11.84 | 0.44 |
| H | 16 | 0.6 | 30.80 | 52.49 | 16.71 | 0.87 |
|  | 16 | 3.22 | 43.99 | 43.03 | 12.97 | 0.54 |
|  | 16 | 4.83 | 55.67 | 34.23 | 10.09 | 0.35 |
|  | 16 | 21.73 | 80.14 | 15.57 | 4.29 | 0.12 |
|  | 16 | 24.03 | 80.05 | 15.65 | 4.30 | 0.12 |
| I | 16 | 0.5 | 30.20 | 53.80 | 15.99 | 0.91 |
|  | 16 | 3.05 | 36.33 | 49.99 | 13.67 | 0.79 |
|  | 16 | 4.62 | 41.97 | 45.55 | 12.48 | 0.62 |
|  | 16 | 21.55 | 72.69 | 21.51 | 5.79 | 0.19 |
|  | 16 | 23.88 | 72.60 | 21.57 | 5.82 | 0.18 |
| J | 40 | 1 | 27.66 | 56.52 | 15.81 | 0.98 |
|  | 40 | 3.15 | 31.29 | 53.94 | 14.76 | 0.85 |
|  | 40 | 23.85 | 39.72 | 47.36 | 12.91 | 0.68 |
| K | 40 | 0.62 | 34.20 | 51.44 | 14.36 | 0.76 |
|  | 40 | 2.65 | 48.32 | 40.50 | 11.18 | 0.46 |
|  | 40 | 23.45 | 81.76 | 14.43 | 3.81 | 0.12 |
| L | 40 | 1.2 | 32.34 | 52.62 | 15.03 | 0.89 |
|  | 40 | 3.35 | 39.99 | 46.74 | 13.26 | 0.67 |
|  | 40 | 24.16 | 74.73 | 19.82 | 5.45 | 0.16 |

For each data point the equilibrium position of the reaction was calculated and then the instantaneous net rate constant for 1233xf conversion, $k'_{xf}$ was calculated In this way for each experiment it was possible to quantify catalyst effectiveness vs time and so derive useful catalyst performance characteristics relating to activity and stability.

For each experiment a plot of $k'_{xf}$ vs time was produced and fitted using the equation:

$$k'_{xf} = b + (a-b)\exp^{-k''t}$$

Where:

a=initial activity b=final activity k″=catalyst activity decay rate and where the initial rate of catalyst activity decay at t=0 hrs=

$$-\frac{k''(a-b)}{\exp^{k''t}}$$

This is exemplified in the table below

| Catalyst | Initial Activity (s$^{-1}$) | Final Activity (s$^{-1}$) | Rate constant decay rate (hr$^{-1}$) | k'$_{xf}$ (24 hr) (s$^{-1}$) | Initial rate of k'$_{xf}$ decay |
|---|---|---|---|---|---|
| 1 | 1.1608 | 0.8447 | 0.3949 | 0.8447 | −0.1248 |
| 2 | 1.0115 | 0 | 0.0105 | 0.7862 | −0.0106 |
| 3* | 1.0941 | 0 | 0.0378 | 0.4416 | −0.0414 |
| 4* | 1.0122 | 0.6018 | 0.2356 | 0.6032 | −0.0967 |
| A | 0.8377 | 0.5329 | 0.1523 | 0.5408 | −0.0464 |
| B | 1.0617 | 0.1095 | 0.1775 | 0.1229 | −0.1690 |
| C | 0.5585 | 0.1432 | 0.7607 | 0.1432 | −0.3159 |
| D | 0.7468 | 0 | 0.0074 | 0.6253 | −0.0055 |
| E | 1.1896 | 0.1195 | 0.3471 | 0.1198 | −0.3714 |
| F | 0.5057 | 0.1693 | 0.3983 | 0.1693 | −0.1340 |
| G | 1.0769 | 0 | 0.0356 | 0.4583 | −0.0383 |
| H | 0.9966 | 0.1174 | 0.2508 | 0.1195 | −0.2205 |
| I | 0.9646 | 0.0713 | 0.0922 | 0.1690 | −0.0824 |
| J | 1.0678 | 0.6747 | 0.2538 | 0.6756 | −0.0998 |
| K | 0.8959 | 0.1143 | 0.3037 | 0.1148 | −0.2374 |
| L | 1.044 | 0.146 | 0.1619 | 0.1644 | −0.1454 |

The catalytic example was repeated under the same conditions as above with the exception that the pressure was increased to 6 bara. The kinetic data obtained is shown in the table below.

| Catalyst | Initial activity (s$^{-1}$) | Final activity (s$^{-1}$) | Rate constant decay rate (hr$^{-1}$) |
|---|---|---|---|
| C | 0.0143 | 0.0000 | 0.0131 |
| 1 | 0.3696 | 0.0000 | 0.0233 |

The catalysts activated according to the method of the invention not only show high initial activity but also show a lower decrease in said activity when compared to catalysts activated in a comparative method.

Pore Size Measurements

Pore sizes of the catalyst were measured according to the BET Ads (4V/A) method. The results are shown in the table below.

| Catalyst | Average pore diameter BET Ads (4V/A) (A) |
|---|---|
| 1 | 142.5 |
| 2 | 151.6 |
| 3* | 146.6 |
| 4* | 146.7 |
| A | 130.4 |
| B | 175.2 |
| C | 133.6 |
| D | 139.6 |
| E | 184.4 |
| F | 142.7 |
| G | 150.3 |
| H | 170.5 |
| I | 144.6 |
| J | 150.5 |
| K | 170.7 |
| L | 144.8 |

Thus, it has been demonstrated how catalyst activation treatments according to the teaching of this patent result in working catalysts with increased porosity and enhanced activity and stability.

The invention claimed is:

1. A method for activating a chromia catalyst comprising zinc oxide, the method comprising:
    a) drying the catalyst at a temperature of from 100° C. to 400° C.;
    b) treating the catalyst in a first activation step with a composition comprising HF at a temperature of from 100° C. to about 500° C.;
    c) treating the catalyst in a second activation step with a composition comprising an oxidant and HF at a temperature of from about 100° C. to about 500° C.

2. The method according to claim 1, wherein the oxidant is selected from the group consisting of air, oxygen (O$_2$), chlorine (Cl$_2$), chlorine monofluoride (ClF), nitrogen trifluoride (NF$_3$).

3. The method according to claim 1, wherein the molar ratio of HF to oxidant is from 1:20 to 20:1.

4. The method according to claim 3, wherein the molar ratio of HF to oxidant is from 15:1 to 1:3, or from 11:1 to 1:1.

5. The method according to claim 1, wherein zinc oxide is present in the catalyst at a level of from 1% wt. to 10% wt., from 2% wt. to 8% wt., or from 3% wt. to 7% wt. based on the total weight of the catalyst.

6. The method according to claim 1, wherein step (b) and/or (c) is carried out at a pressure of from 0.1 bara to 20 bara, or from 3 bara to 10 bara.

7. The method according to claim 1, wherein step (b) and/or (c) is carried out over an extended period of time.

8. The method according to claim 1, wherein step (b) and/or (c) is carried out at a temperature of from about 200° C. to about 500° C., or from about 250° C. to about 475° C.

9. The method according to claim 1, wherein step (b) and/or (c) is conducted at a temperature of from about 300° C. to 460° C., or from about 310° C. to about 450° C.

10. The method for activating a catalyst according to claim 1, wherein the zinc oxide is present in the catalyst at a level of from 1% wt. to 10% wt., wherein the catalyst has a total pore volume equal to or greater than 0.3 cm$^3$/g and a mean pore diameter greater than or equal to 100 A, wherein the pore volume is measured using N$_2$ adsorption porosimetry and the mean pore diameter is measured using N$_2$ BET adsorption porosimetry.

11. The method according to claim 10, further comprising a catalyst preparation process comprising:
    preparing a metal salt solution and a hydroxide solution;
    combining the solutions at a pH of greater than 7.5 in order to precipitate a metal hydroxide(s);
    drying the precipitated metal hydroxide(s);
    calcining the metal hydroxide(s) to form a metal oxide(s).

12. The method according to claim 10, wherein the catalyst is amorphous, or from 0.1 to 50% by weight of the catalyst is in the form of one or more crystalline compounds of chromium and/or one or more crystalline compounds of zinc.

13. The method according to claim 10, wherein the oxidant is selected from the group consisting of air, oxygen (O2), chlorine (Cl2), chlorine monofluoride (ClF), nitrogen trifluoride (NF3).

14. The method according to claim 10, wherein the molar ratio of HF to oxidant is from 1:20 to 20:1, from 15:1 to 1:3, or from 11:1 to 1:1.

15. The method according to claim 10, wherein step (b) and/or (c) is carried out at a pressure of from 0.1 bara to 20 bara, or from 3 bara to 10 bara.

16. The method according to claim 10, wherein step (b) and/or (c) is carried out over an extended period of time.

17. The method according to claim 10, wherein step (b) and/or (c) is carried out at a temperature of from about 200° C. to about 500° C., or from about 250° C. to about 475° C.

18. The method according to claim 17, wherein step (b) and/or (c) is conducted at a temperature of from about 300° C. to 460° C., or from about 310° C. to about 450° C.

19. A method comprising a fluorination and/or hydrofluorination of a halogenated hydrocarbon in the presence of the catalyst prepared according to claim 1.

20. The method according to claim 19, wherein the halogenated hydrocarbon is a (hydro)haloalkene.

21. The method according to claim 20, wherein the (hydro)haioalkene is a $C_{2-7}$(hydro)haloalkene.

22. The method according to claim 21, wherein the $C_{2-7}$(hydro)haloalkene is a $C_{2-7}$(hydro)chlorofluoroalkene.

23. The method according to claim 22, wherein the $C_{2-7}$(hydro)chlorofluoroalkene is 2-chloro-3,3,3-trifiuoropropene (1233xf).

24. A process for preparing a fluorinated hydrocarbon, the process comprising reacting an optionally halogenated hydrocarbon with hydrogen fluoride in the presence of the catalyst produced in accordance with the method of claim 1, wherein the process is carried out in vapour phase.

* * * * *